United States Patent [19]

Takiguchi et al.

[11] 4,346,171

[45] Aug. 24, 1982

[54] FERMENTATION PROCESS FOR PRODUCING COMPOUND HAVING ANTHELMINTIC AND ACARICIDAL ACTIVITIES

[75] Inventors: Yo Takiguchi; Hiroshi Mishima, both of Tokyo; Shinjiro Yamamoto, Shiga; Michiya Terao, Tokyo, all of Japan

[73] Assignee: Sankyo Company, Limited, Tokyo, Japan

[21] Appl. No.: 179,479

[22] Filed: Aug. 18, 1980

[30] Foreign Application Priority Data

Aug. 23, 1979 [JP] Japan .................................. 54-107550

[51] Int. Cl.$^3$ .............................................. C12P 17/18
[52] U.S. Cl. ..................................... 435/119; 424/279
[58] Field of Search ......................................... 435/119

[56] References Cited

U.S. PATENT DOCUMENTS

| | | |
|---|---|---|
| 3,966,914 | 6/1976 | Aoki et al. . |
| 3,984,564 | 10/1976 | Aoki et al. . |
| 3,992,527 | 11/1976 | Aoki et al. . |
| 3,992,551 | 11/1976 | Aoki et al. . |
| 3,992,552 | 11/1976 | Aoki et al. . |
| 3,998,699 | 12/1976 | Aoki et al. . |
| 4,171,314 | 10/1979 | Chabala et al. . |
| 4,173,571 | 11/1979 | Chahala et al. . |
| 4,206,205 | 10/1980 | Mrozik et al. . |

FOREIGN PATENT DOCUMENTS

2348970 11/1977 France .
1573955 8/1980 United Kingdom .

OTHER PUBLICATIONS

"Avermectins", Albers–Schönberg et al., Paper No. 464, Publication at Interscience Conference (Oct. 4, 1978).
Chabala et al., Paper No. 7, Medicinal Chemistry Section, 178th American Chemical Society National Meeting of Sep. 9–14, 1979.
Mrozik et al., Paper No. 259, Organic Section, 178th American Chemical Society National Meeting of Sep. 9–14, 1979.

*Primary Examiner*—Alvin E. Tanenholtz
*Attorney, Agent, or Firm*—Frishauf, Holtz, Goodman & Woodward

[57] ABSTRACT

A new compound, named "Compound B-41D", has the formula:

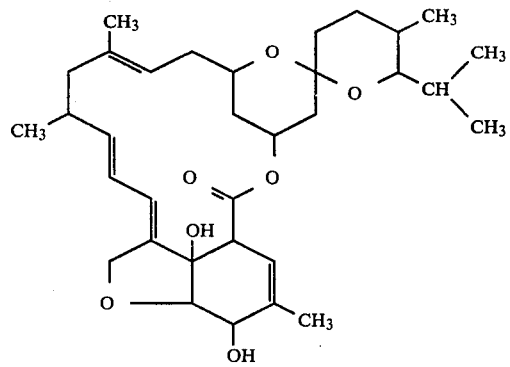

and can be prepared by cultivating a microorganism of the genus Streptomyces, especially Streptomyces strain B-41-146. Compound B-41D has valuable acaricidal and anthelmintic activities.

11 Claims, 3 Drawing Figures

FERMENTATION PROCESS FOR PRODUCING COMPOUND HAVING ANTHELMINTIC AND ACARICIDAL ACTIVITIES

BACKGROUND OF THE INVENTION

The present invention relates to a new compound, designated B-41D, which can be prepared by the cultivation of microorganisms of the genus Streptomyces and which has valuable acaricidal and anthelmintic activities.

We have disclosed in our British Patent Specification No. 1,390,336 that microorganisms of the genus Streptomyces, and especially Streptomyces strain B-41-146 (Ferm 1438), can produce an antibiotic substance B-41, which can be separated into 9 different constituents, which are designated in that Specification as $A_1$, $A_2$, $A_3$, $A_4$ $B_1$, $B_2$, $B_3$, $C_1$ and $C_2$. Subsequently, it was discovered that four other compounds of similar structure could be obtained by cultivating the same strain of Streptomyces. The structure and properties of all thirteen compounds are described, inter alia, in J. Antibiotics 29 (3), pages 76-14 to 76-16 and 29 (6), pages 76-35 to 76-42.

Subsequently, a series of compounds structurally similar to the compounds making up substance B-41 were discovered and named the "avermectins" (or "C-076"). The avermectins and derivatives thereof are disclosed in: U.S. Patent Application Ser. No. 678,328; Antimicrobial Agents and Chemotherapy, 15 No. 3, pages 361-367 (1979), U.S. Pat. No. 4,206,205, European Patent Application No. 0,001,689; U.S. Pat. No. 4,171,314; U.S. Pat. No. 4,173,571; European Patent Application No. 0,002,615; and European Patent Application No. 0,008,184.

In British Pat. No. 1,390,336, it was disclosed that the complex of substances B-41 together and individually had insecticidal and acaricidal properties. Subsequently, in U.S. Pat. No. 4,144,352, it was disclosed that these and related substances also had anthelmintic activity. In U.S. Pat. No. 4,144,352, the B-41 substances were referred to as "milbemycins". For clarity, we, too, in this Specification refer to the prior art compound as "milbemycins", although it will be appreciated that certain of these compounds are identical to those compounds making up substance B-41, as described in British Patent Specification No. 1,390,336. Various milbemycin derivatives are disclosed in U.S. Pat. No. 4,093,629 and No. 4,134,973.

The thirteen milbemycin compounds which can be produced by cultivation of Streptomyces B-41-146 have the formulae (I), (II) and (III). the structure of milbemycins $\alpha_{1-10}$ is given by formula (I):

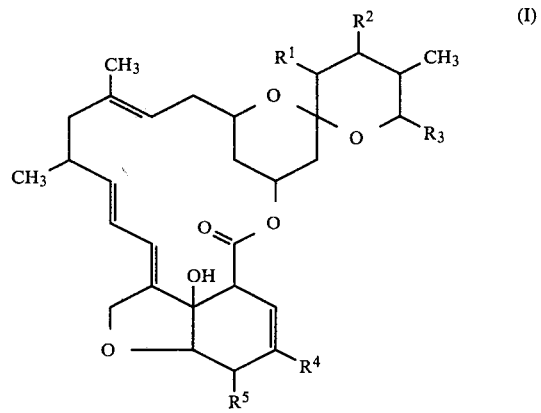

The definitions of the groups $R^1$, $R^2$, $R^3$, $R^4$ and $R^5$ are given in the following Table 1, which also shows, where appropriate, the corresponding B-41 designation, as used in British Patent Specification No. 1,390,336. Of the thirteen known compounds produced by Streptomyces strain B-41-146, the milbemycins $\alpha_{1-10}$ are closest in structure to the new Compound B-41D of the present invention and the appropriate definitions of the groups $R^1$-$R^5$ as applied to Compound B-41D are also given in Table 1.

In this Table, the following abbreviations are used:
MH means a 2-methylhexanoyloxy group of formula

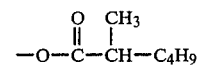

PC means a 2-pyrrolylcarbonyloxymethyl group of formula

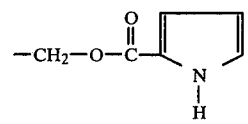

TABLE 1

| Milbemycin | $R^1$ | $R^2$ | $R^3$ | $R^4$ | $R^5$ | B-41 |
|---|---|---|---|---|---|---|
| $\alpha_1$ | H | H | $CH_3$ | $CH_3$ | OH | $A_3$ |
| $\alpha_2$ | H | H | $CH_3$ | $CH_3$ | $OCH_3$ | $B_2$ |
| $\alpha_3$ | H | H | $C_2H_5$ | $CH_3$ | OH | $A_4$ |
| $\alpha_4$ | H | H | $C_2H_5$ | $CH_3$ | $OCH_3$ | $B_3$ |
| $\alpha_5$ | OH | MH | $CH_3$ | $CH_3$ | OH | $A_2$ |
| $\alpha_6$ | OH | MH | $CH_3$ | $CH_3$ | $OCH_3$ | $B_1$ |
| $\alpha_7$ | OH | MH | $C_2H_5$ | $CH_3$ | OH | — |
| $\alpha_8$ | OH | MH | $C_2H_5$ | $CH_3$ | $OCH_3$ | — |
| $\alpha_9$ | H | H | $CH_3$ | PC | OH | $C_1$ |
| $\alpha_{10}$ | H | H | $C_2H_5$ | PC | OH | $C_2$ |
| — | H | H | $CH(CH_3)_2$ | $CH_3$ | OH | D |

The structures of milbemycins $\beta_1$ and $\beta_2$ are given in formula (II):

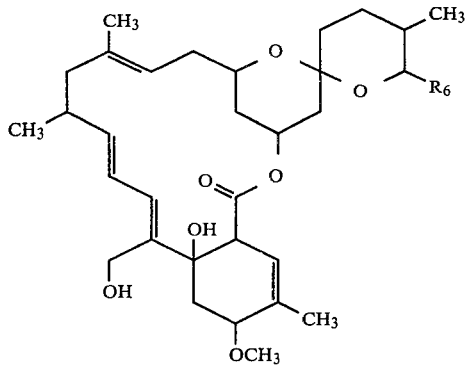

(II)

in which $R^6$ represents, for milbemycin $\beta_1$, a methyl group and, for milbemycin $\beta_2$, an ethyl group. Milbemycin $\beta_1$ corresponds to Compound B-41A$_1$ of British Patent Specification No. 1,390,336.

The structure, of milbemycin $\beta_3$ is given by formula (III):

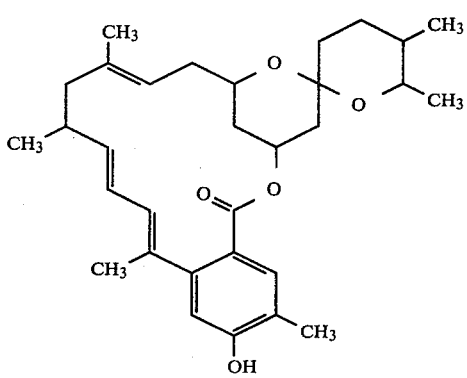

(III)

BRIEF SUMMARY OF INVENTION

It is an object of the present invention to provide, as a new composition of matter, Compound B-41D, which has the formula:

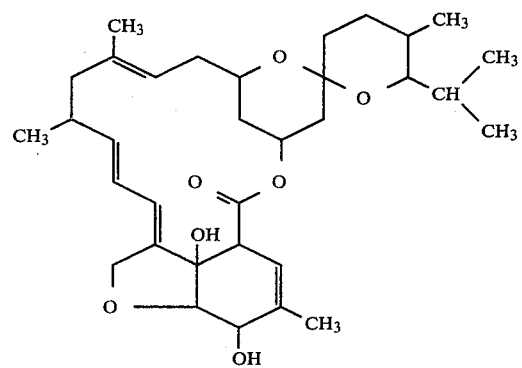

It is a further object of the invention to provide a method of preparing Compound B-41D by cultivating a Compound B-41D-producing microorganism of the genus Streptomyces in a culture medium therefor and separating Compound B-41D from the culture medium.

It is a still further object of the invention to provide an acaricidal or anthelmintic composition comprising Compound B-41D in admixture with a carrier, diluent or adjuvant.

It is another object of the invention to provide a method for the treatment of helminthic infections by administering to an animal (including humans) infected with helminths an effective amount of Compound B-41D.

It is yet another object of the invention to provide a method for controlling mites by applying effective amount of Compound B-41D to an animal, plant or environment.

DETAILED DESCRIPTION OF INVENTION

Figure 1:
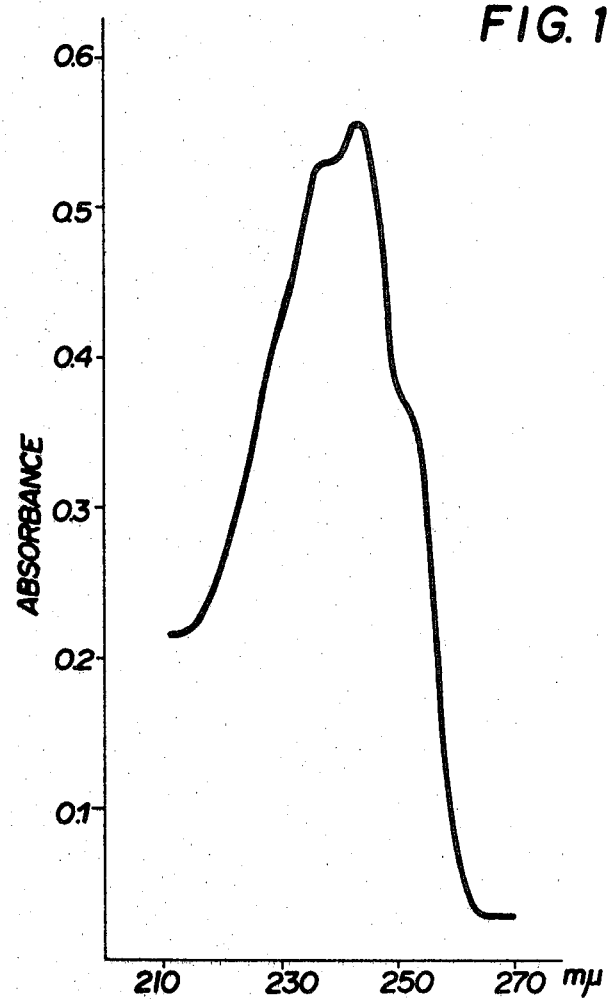
Figure 2:
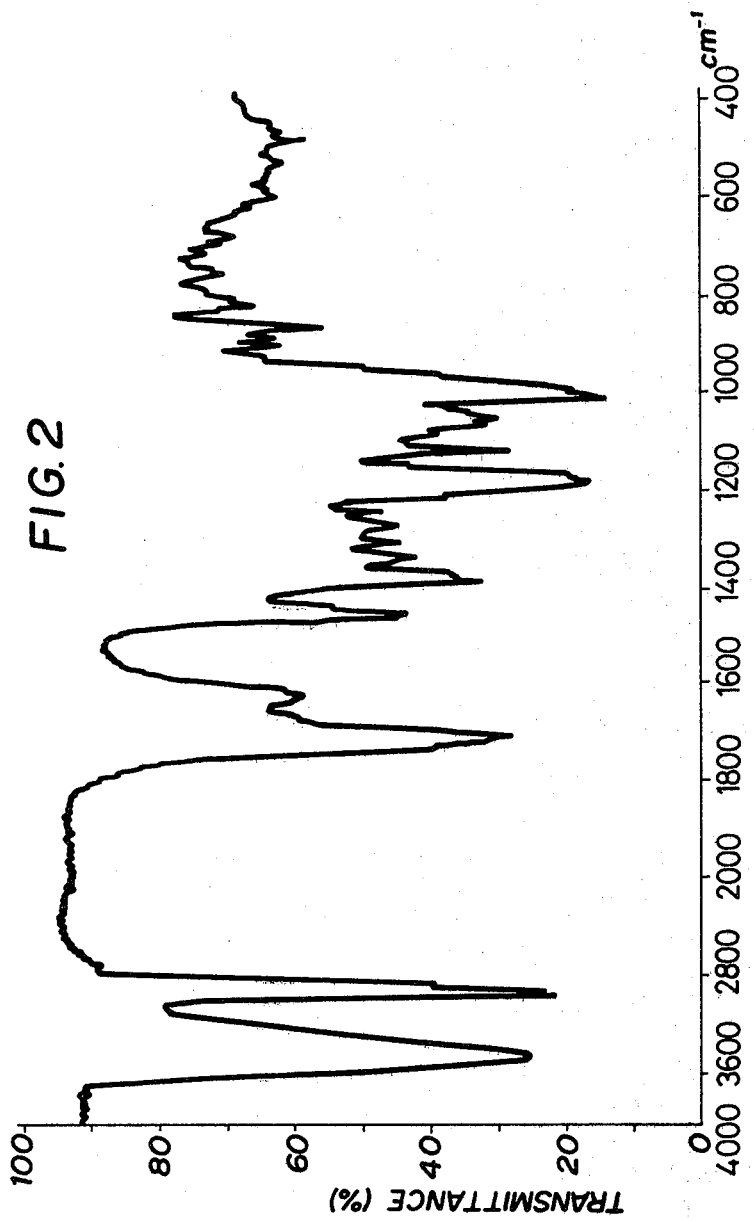
Figure 3:
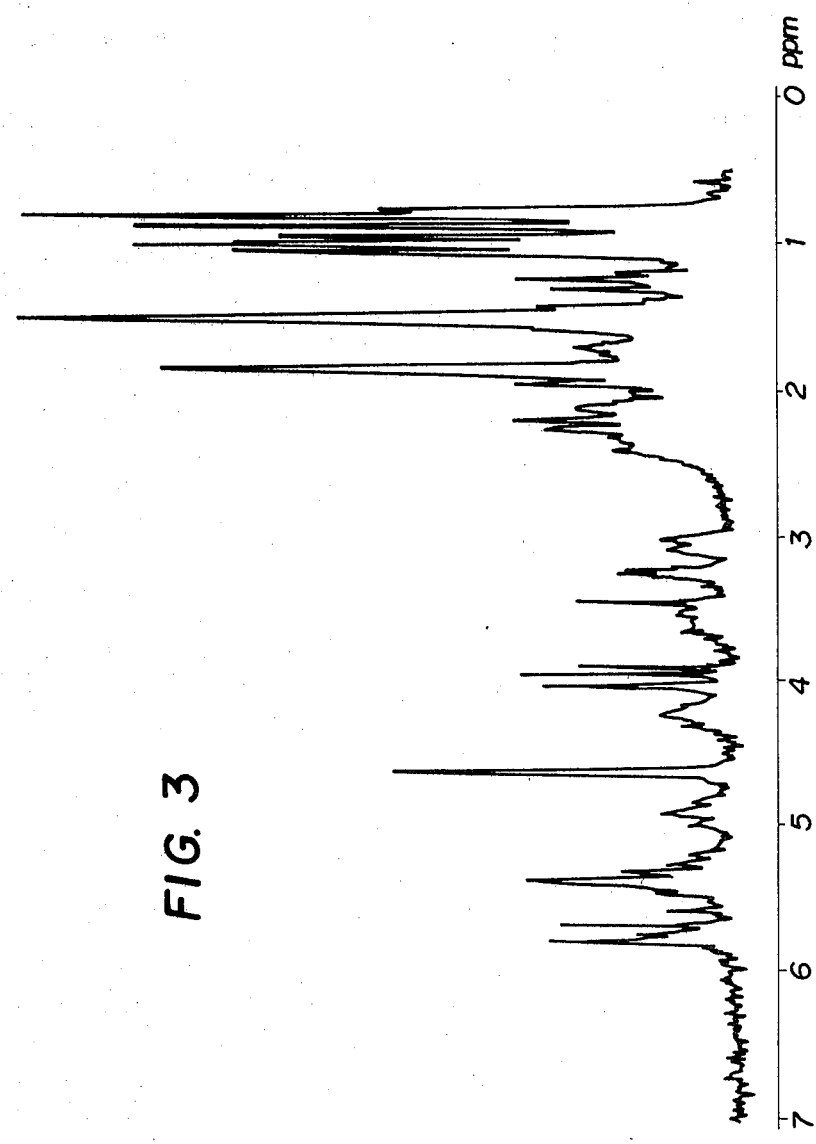

Compound B-41D has the formula given above and the following physical and chemical characteristics:
(1) Appearance: amorphous powder or crystals.
(2) Elemental Analysis:
Calculated for $C_{33}H_{47}O_7$:
C, 71.09%; H, 8,80%; O, 20.11%.
Found: C, 71.40%; H, 8,82%; O, 20.22%.
(3) Molecular Weight: 556.
(4) Ultraviolet Absorption Spectrum: as shown in FIG. 1 of the accompanying drawings. Absorption maxima at 237 m$\mu$ (shoulder, $\epsilon=20400$) and 243 m$\mu$ ($\epsilon=30500$).
(5) Infrared Absorption Spectrum (KBr tablet): as shown in FIG. 2 of the accompanying drawings.
(6) Nuclear Magnetic Resonance Spectrum at 100 MHz in CDCl$_3$ using tetramethylsilane as internal standard: as shown in FIG. 3 of the accompanying drawings.
(7) Solubility: Readily soluble in ethyl acetate, acetone, ethanol and methanol. Barely soluble in water.
(8) Thin layer chromatography on silica gel (Kieselgel 60 F$_{254}$, Merck Co.) developed with a 18:82 by volume mixture of dioxan and carbon tetrachloride: Rf value=0.40.

Compound B-41D can be prepared by cultivating a microorganism of the genus Streptomyces, but especially Streptomyces strain B-41-146 (Ferm 1438). The morphological, cultural and physiological characteristics and taxonomic properties of strain B-41-146 are described in detail in British Patent Specification No. 1,390,336. This strain has been deposited with the Fermentation Research Institute, Agency of Industrial Science and Technology, Ministry of International Trade and Industry, Japan, Whence it is available under the accession number Ferm 1438 (also known as "Bikoken-kinki 1438").

As is well-known, Streptomyces tend to mutate both naturally and by application of such artificial operations as, for example, ultraviolet irradiation, ionizing radiation or chemical treatment. This is also the case with the B-41-146 strain used in the process of the present invention. Consequently, any Compound B-41D-producing mutant of the described Streptomyces strain B-41-146 may be used to produce the compound of the present invention.

The compound of the present invention can be obtained by culturing Streptomyces strain B-41-146 in a suitable medium and then recovering the resulting compound from the fermentation broth. Any known nutrient heretofore used for the cultivation of microorganisms of the genus Streptomyces may be used. In general, as is well-known, such a culture medium should contain at least a source of assimilible carbon and a source of assimilible nitrogen. Suitable carbon sources include glucose, sucrose, starch, glycerin, malt extract, molasses and soybean oil. Particularly preferred as the carbon source is glucose, preferably in an amount of up to 8%, more preferably from 6 to 8%, w/v of the culture medium. In addition to the glucose, it is preferred to use one or more of lactose, maltose and corn starch (preferably in an amount of from 0.5 to 2.0% w/v) as an additional carbon source. In order to maintain a constant pH, it is preferred to add extra glucose throughout the cultivation.

Suitable nitrogen sources include soybean meal, wheat germ, meat extract, peptone, fresh yeast, corn steep liquor, ammonium sulphate and ammonium nitrate. Particularly preferred as the nitrogen source is a combination of soybean meal and skimmed milk, preferably from 0.5 to 1.0% w/v of soybean meal and from 1.0 to 2.0% w/v of skimmed milk. If desired, an amino acid (e.g. glycine or arginine) may be incorporated in the culture medium.

If desired, inorganic salts, such as calcium carbonate, sodium chloride, potassium chloride or phosphates, may be added, as may also be added other organic or inorganic substances designed to aid microbial growth and promote the production of the desired compound.

Surprisingly good yields of Compound B-41D may be obtained by using a culture medium containing from 6 to 8% w/v glucose; from 0.5 to 2% w/v of lactose and/or maltose and/or corn starch; from 0.5 to 1.0% w/v soybean meal; and from 1.0 to 2.0% w/v skimmed milk.

Although any known method of culturing the Streptomyces strain B-41-146 may be employed, as with the case of fermentation to provide other biologically active substances, liquid culture, and particularly submerged culture, is the most suitable method. The culture is preferably conducted aerobically and at a temperature which may vary over a wide range, suitably from 22° to 30° C. and preferably about 28° C. The production of the desired Compound B-41D reaches a maximum after 5 to 10 days culture, either by shaking or in a tank.

The determination of Compound B-41D in the culture broth may be effected as follows. A known amount, say 3 g, of the culture broth is introduced into a small test tube, to which 10 ml of acetone is then added and the mixture is extracted by shaking and then centrifuged. To the supernatant solution thus obtained is added acetone to a total volume of 10 ml. The resulting solution is applied at a predetermined position on a thin layer chromatography plate (silica gel, e.g. Kieselgel 60 $F_{254}$, available from E. Merck) in an amount of, for example, 10–20 $\mu$ liters. The plate is then developed for 4 hours with a 18:82 by volume mixture of dioxan and carbon tetrachloride. The sample is then measured by means of a dual wavelength thin layer chromatography scanner at a wavelength of 245 m$\mu$ (the blank at 380 m$\mu$). The amount of absorbance is compared with that of a known standard sample of the compound, from which the amount of Compound B-41D can be calculated.

Compound B-41D can be recovered from the culture broth using a natural adsorbent (such as active carbon, alumina or silica gel), a synthetic adsorbent (such as Diaion HP-20, a product of Mitsubishi Chemical Industries, Limited), an absorbent (such as Avicel, a product of Asahi Chemical Industry Co., Limited or filter paper), an ion exchange resin, an ion exchange gel filter or the like. However, recovery can most effectively be conducted by the following method.

First, the fermentation broth is filtered using a filter aid (such as diatomaceous earth) to obtain a cake, which is then subjected to methanolic extraction in order to dissolve the desired substance in an aqueous methanolic solution. Water is then added to the aqueous methanolic solution and the resulting solution is extracted with hexane. The hexane phase is separated and concentrated by evaporation under reduced pressure to give an oily substance containing the desired Compound B-41D. This oily substance is placed onto a column containing silica gel (e.g. Wakogel C-200) and eluted with a suitable mixture, e.g. 95:5 by volume, of hexane and acetone to collect fractions containing the desired compound. These fractions are concentrated by evaporation under reduced pressure, again giving an oily substance, which is dissolved in a small amount of methanol and added to a column of Sephadex LH-20 (a trade mark for a product of Pharmacia Co.) and eluted with methanol. The fractions containing the desired substance are collected, the solvent is removed and the residue is dissolved in a small amount of methanol. Water is added and the mixture is left to stand at room temperature. The resulting Compound B-41D is obtained in the form of a foam or bubbles which, on breaking, give an amorphous powder. When recrystallized from a 20:1 by volume mixture of hexane and ethyl acetate, Compound B-41D is obtained in the form of small needles melting at 186°–188° C.

Although the Compound B-41D may be separated and purified for use, e.g. as described above, it is also possible to discontinue the purification procedure at any desired stage and to use the crude product, which contains a mixture of milbemycins as well as Compound B-41D. If a mixture containing two or more such compounds is used without complete separation, it is sufficient that it should be so purified as to obtain a 100% acaricidal effect at a concentration of 5 ppm. The content of Compound B-41D in the crude mixture in this case is preferably at least 25% by weight, and more preferably about 50% by weight, the remainder being impurities from the broth and other milbemycins.

The compound of the present invention has superior acaricidal activity against adults and eggs of such mites as the two-spotted spider mite (*Tetranychus urticae*), the European red mite (*Panonychus ulmi*), the citrus red mite (*Panonychus citri*) and rust mites (e.g. of the genera Aculops or Aculus), which are parasitic on fruits, vegetables and flowers. It is also active against mites of the genera Ixodidae, Dermanyssidae and Sarcoptidae, which are parastic on animals. The compound is also highly active against such ectoparasites as Oestrus, Lucilia, Hypoderma, Gasterophylus, fleas, lice etc., as well as insects of sanitary importance (such as cockroaches or flies) and other horticulturally and agriculturally damaging insects, such as aphides and larvae of insects of the order Lepidoptera. Furthermore, it is active against nematodes, such as those of the genus Meloidogyne, and bulb mites such as those of the genus Rhizoglyphus, which are found in the soil.

For use as an acaricidal or insecticidal preparation, the compound of the invention is preferably diluted with a carrier, to form preparations such as powders, coarse powders, granules, fine granules, wettable powders, emulsifiable concentrates or oils.

The carrier used to prepare such preparations may be synthetic or natural, inorganic or organic and, in general, any carrier which is conventionally added to insecticides or acaricides in order to make it easier for the active ingredient to reach the object to be treated (e.g. plant, mite or harmful insect) or to facilitate storage, transportation or handling of the active ingredient may be used.

Examples of suitable solid carriers include: inorganic substances, such as clay, talc, diatomaceous earth, kaolin, bentonite, calcium carbonate or synthetic calcium silicate; natural or synthetic resins, such as coumarone resins, alkyd resins and polyvinyl chlorides; waxes, such as carnauba wax and paraffin wax; shells of nuts, such as walnut shells; or soybean meal.

Examples of suitable liquid carriers include: water; alcohols, such as ethanol or isopropanol; glycols, such as ethylene glycol, glycol ethers, such ethylene glycol monophenyl ether or diethylene glycol monoethyl ether; ketones, such as acetone, methyl isobutyl ketone, cyclohexanone, acetophenone or isophorone; ethers, such as tetrahydrofuran or dioxan; aromatic hydrocarbons, such as benzene, toluene, xylene or methylnaphthalene; chlorinated hydrocarbons, such as trichloroethylene and carbon tetrachloride; and low, medium and high boiling point petroleum fractions containing kerosine, light oils or aromatic hydrocarbons.

The compound of the invention may also be formulated as an aerosol, in which case the carrier would be a propellant. Suitable propellants include gaseous fluorocarbons (including those sold under the trade mark "Freon"), liquified petroleum gas, dimethyl ether and vinyl chloride monomer.

If desired, the preparation may also include a surface active agent for the purpose of emulsifying, dispersing, wetting or spreading the active compound and such a surface active agent may be either ionic or nonionic. Examples of suitable anionic surface active agents include: the sodium and calcium salts of lignosulphonic acid; the sodium and potassium salts of oleic acid; the sodium salt of laurylsulphonic acid; and the sodium and calcium salts of dodecylbenzenesulphonic acid. Examples of suitable cationic surface active agents include the higher aliphatic amines and condensates of the higher aliphatic amines with ethylene oxide. Examples of suitable non-ionic surface active agents include: glycerides of fatty acids; sucrose esters of fatty acids; condensates of ethylene oxide with higher aliphatic alcohols; condensates of ethylene oxide with higher fatty acids; condensates of ethylene oxide with alkylphenols or alkylnaphthols; and copolymers of ethylene oxide with propylene oxide.

The acaricidal or insecticidal preparation of the present invention may alternatively or in addition contain a protective colloid (such as gelatin, gum arabic, casein, polyvinyl alcohol or carboxymethylcellulose) or a thixotropic agent (such as sodium polyphosphorate or bentonite). The preparation may also contain other compounds having an acaricidal activity, for example 2-(1-methylpropyl)-4,6-dinitrophenyl-β,β-dimethyl acrylate, di-(p-chlorophenyl)cyclopropylcarbinyl, N'-(4-chloro-2-methylphenyl)-N,N-dimethylformamidine, 2,4,4',5-tetrachlorodiphenyl sulphone, 1,1-bis(p-chlorophenyl)-2,2,2-trichloroethanol, 2-sec-butylphenyl-N-methylcarbamate, m-tolyl-N-methylcarbamate or mineral oil, in order to increase the activity of the preparation; in some cases, a synergistic effect can be expected.

It is, of course, also possible to use the compound of the present invention in admixture with other fungicides, herbicides, plant growth regulators, attractants or fertilizers.

Compound B-41D is also highly active as a parasiticide for the treatment of human beings and other animals. The diseases commonly referred to as "parasitism" are caused in diseased animal hosts by metazoan organisms commonly known as the Helminthes. The parasites can attach livestock, poultry and pet animals (such as pigs, sheep, goats, cows, horses, dogs, cats, and chickens) as an epidemic and can cause grave economic damage. Among the Helminthes, a group of parasites known as the Nematodae in particular may spread among various animals and often cause serious infections. Typical genera of the Nematodae which will infect the animals described above are:

Haemonchus;
Trichostrongylus;
Ostertagia;
Nematodirus;
Cooperia;
Ascaris;
Bunostomum;
Oesophagostomum;
Chabertia;
Trichuris;
Strongylus;
Trichonema;
Dictyocaulus;
Capillaria;
Strongyloides;
Heterakis;
Toxocara;
Ascaridia;
Oxyuris;
Ancylostoma;
Uncinaria;
Toxascaris; and
Parascaris.

Some of the parasites of the genera Nematodirus, Cooperia and Oesophagostomum attack the intestines, whilst parasites of the genera Hemonchus and Ostertagia attack the stomach, and parasites of the genus Dictyocaulus are found in the lungs. Parasites of the family Filariidae or Setariidae are found in the heart, the blood vessels and tissues and organs such as the subcutaneous tissues and lymphatic vessels.

The compound of the present invention has a broad spectrum activity against many endoparasites in various animals and, for example, it is effective against parasites of the genera Dirofilaria in dogs, Nematospiroides, Syphacia and Aspiculuris in the rhodentias.

Compound B-41D is also useful against various parasites which are infectious to human beings. Typical of such parasites which may be found in the digestive tracts of human beings are parasites of the genera:

Ancylostoma;
Necator;
Ascaris;
Strongyloides;
Trichinella;
Capillaria;
Trichuris; and
Enterobius.

Other medically significant parasites which are found in the blood, tissues or in organs other than the digestive tracts are of the genera Wuchereria, Brugia, Onchocerca and Loa of the family Filariidae, Dracunculus of the family Drachunculidae and Stronglylodies and Trichinella, which are extraordinary for being normally ectoparasitic but often are endoparasitic in the digestive tract.

When Compound B-41D is to be used as a parasiticide for humans and other animals, it is preferably administered orally as a drink or capsule. It may be formulated as an aqueous solution, or a solution in another suitable nontoxic solvent, or as a suspension or dispersion incorporating a suspension aid and a wetting agent, such as bentonite, or other constituents. In general, the drink would also contain a defoaming agent. We normally prefer that the drink should contain the active compound in an amount of from 0.01 to 0.5% by weight, and more preferably from 0.01 to 0.1% by weight.

It is also possible to administer Compound B-41D in unit dosage form, e.g. in the form of dry solid capsules, pills or tablets containing a predetermined amount of the active compound. These formulations can be obtained by homogeneously mixing the active compound with one or more finely pulverized materials, such as diluents, filling agents, disintegrators or binding agents (e.g. starch, lactose, talc, magnesium stearate or vegetable gum). The weight and content of active ingredient in such unit dosage forms may vary widely, depending upon the type of animal to be treated, the degree of infection, the kind of parasite and the body weight of the animal.

Compound B-41D may be administered to animals by uniformly dispersing it in their feed or it may be used as a top dressing or in the form of pellets. In order to achieve satisfactory antiparasitic activity, it is desirable that the final feed should contain the active compound in an amount of from 0.0001 to 0.02% by weight.

Compound B-41D may also be dissolved or dispersed in a liquid carrier and administered parenterally to animals by injection into the proventriculus, the muscles, the lungs or under the skin. For parenteral administration, the carrier used is preferably a vegetable oil, such as peanut oil or cottonseed oil. For parenteral administration, the active compound is preferably present in an amount of from 0.05 to 50% by weight of the formulation.

Topical administration of Compound B-41D is also possible, in which case the active compound is preferably mixed with a suitable carrier, such as dimethyl sulphoxide or a hydrocarbon solvent. The resulting formulation can be directly applied to the outer skin of the animals, e.g. by spraying.

The optimum amount of Compound B-41D to achieve best results will vary depending upon the kind of animal to be treated, the type of parasitic infection and the degree of infection, but in general we prefer to administer from 0.01 to 100 mg/kg body weight of the animal, and more preferably, in the case of oral administration, from 0.1 to 50 mg/kg. The compound may be administered as a single dose or in divided doses and it is normally only necessary to treat the animal for a relatively short period of time, e.g. from 1 to 5 days.

The invention is further illustrated by the following Examples, of which Examples 1 and 2 illustrate the preparation of Compound B-41D, Examples 3-6 illustrate acaricidal compositions containing it, Examples 7-9 illustrate its acaricidal activity and Examples 10-14 illustrate its anthelmintic activity.

EXAMPLE 1

Preparation of Compound B-41D 600 ml of a pre-culture medium containing 2% w/v glucose, 1% w/v soybean meal, 0.5% w/v corn steep liquor (a product of Corn Products Co.) and 0.2% sodium chloride were placed in an Erlenmeyer flask of 2 liters capacity. A loopful of spores of Streptomyces strain B-41- 146 was inoculated into the medium and then cultivated for 48 hours at 27° C. At the end of this time, the contents of two such 2 liter Erlenmeyer flasks were transferred into a jar fermenter of 30 liters capacity, which already contained 20 liters of a thoroughly sterilized culture medium containing 4% w/v glucose, 1% w/v soybean meal, 0.5% w/v corn starch, 1% w/v skimmed milk, 0.2% w/v corn steep liquor and 0.3% sodium chloride. The pH value of the medium was 7.2–7.5 before sterilization. The culture was then incubated at 28° C. under an internal pressure of 0.5 kg/cm$^2$ for 10 days.

At the end of this time, 20 liters of the culture broth were adjusted to a pH value of 3 by the addition of sulphuric acid and then, after adding 1 kg of Celite (trade mark) filter aid, the mixture was filtered under pressure to give about 3 kg of a cake. This cake was extracted with 15 liters of methanol and the extract was filtered. 15 liters of the methanolic solution thus obtained were diluted with 5 liters of water and extracted with 20 liters of hexane. The hexane solution thus obtained was dried over anhydrous sodium sulphate and then concentrated by evaporation under reduced pressure on a water bath maintained at 40°-45° C. to give 22 g of an oily substance.

This oily substance was dissolved in 30 ml of hexane and adsorbed on a column containing 2 kg of silica gel equilibrated with hexane. The column was eluted with a 95:5 by volume mixture of hexane and acetone. 2 liters of a fraction containing the desired compound were obtained and this was concentrated under reduced pressure on a water bath maintained at 40°-45° C. to give 550 mg of an oily substance. This substance was dissolved in 1 ml of methanol and the solution placed on a column containing 200 ml of Sephadex (trade mark) LH-20, which had been equilibrated with methanol. The column was then eluted with methanol to give 65 ml of a fraction containing the desired compound. This raction was concentrated by evaporation under reduced pressure at 45° C. and the resulting residue was then dissolved in 2 ml of methanol and the methanolic solution was diluted with 2 ml of water. The mixture was left standing at room temperature to give 110 mg of Compound B-41D in the form of an amorphous powder having the properties heretofore described.

EXAMPLE 2

Preparation of Compound B-41D

A 2 liter flask containing 600 ml of a preculture medium containing 1% w/v sucrose, 0.35% w/v polypeptone and 0.05% w/v dipotassium orthophosphate was inoculated with a loopful of spores of Streptomyces strain B-41-146 and then the microorganism was cultivated for 48 hours at 27° C. The contents of three such flasks were then transferred into a 600 liter fermentation tank into which had previously been charged 300 liters of a thoroughly sterilized culture medium containing 8% w/v glucose, 1% w/v soybean meal, 0.5% w/v corn starch, 1% w/v skimmed milk, 0.2% w/v corn steep liquor, 0.3% w/v sodium chloride and 0.05 w/v calcium carbonate. The pH of the medium was maintained at 7.2-7.5. Cultivation was then effected at 28° C., under agitation at 150-200 rpm and an internal pressure of 0.5-1 kg/cm$^3$ for 12 days.

At the end of this time, the amount of Compound B-41D in the medium was 180 μg/ml. 300 liters of the resulting culture medium were adjusted to a pH value of 3 by the addition of sulphuric acid and then 15 kg of Celite filter aid were added and the mixture was filtered under pressure, giving 40 kg of a cake. This cake was extracted with 200 liters of methanol and filtered. 150 liters of water were added to the methanolic extract and the resulting mixture was extracted twice, each time with 250 liters of hexane. The resulting hexane solution was dried over anhydrous sodium sulphate and then concentrated by evaporation under reduced pressure in a water bath maintained at 40°-45° C., to give 350 g of an oil.

This oil was dissolved in 400 ml of hexanes and adsorbed on a column containing 3 kg of silica gel which had previously been equilibrated with hexane. The column was eluted with a 95:5 by volume mixture of hexane and acetone, giving 8 liters of an eluate fraction containing the desired compound. This fraction was concentrated by evaporation under reduced pressure over a water bath maintained at 40°-45° C. to give 33 g of crude crystals. These crystals were dissolved in a 20:1 by volume mixture of hexane and ethyl acetate, from which they were recrystallized to give 17.4 g of Compound B-41D in the form of colourless needles melting at 186°-188° C. and having the properties heretofore described.

EXAMPLE 3

Powder

10 Parts by weight of Compound B-41D in the form of an amorphous powder were added to and homogeneously mixed with 5 parts of white carbon. To the resulting mixture were then added 50 parts by weight of talc and 35 parts by weight of clay and this was then homogeneously mixed and then pulverized three times in an impact-type pulverizer and then again homogeneously mixed to give a powder.

EXAMPLE 4

Wettable Powder

40 Parts by weight of Compound B-41D in the form of an amorphous powder were mixed with 20 parts by weight of white carbon. 5 Parts by weight of sodium dodecylbenzene sulphonate, 2 parts by weight of polyvinyl alcohol and 33 parts by weight of clay were added and mixed homogeneously. The mixture was then pulverized three times using an impact-type pulverizer, after which it was again mixed homogeneously to give a wettable powder.

EXAMPLE 5

Emulsifiable Concentrate

3 Parts by weight of Compound B-41D in the form of an amorphous powder, 7 parts by weight of polyoxyethylene nonylphenyl ether, 3 parts by weight of calcium dodecylbenzene sulphonate and 87 parts by weight of xylene were mixed and filtered to give a solution which could be used as an emulsifiable concentrate.

EXAMPLE 6

Oil-based Preparation 10 parts by weight of Compound B-41D in the form of an amorphous powder were dissolved in 10 parts by weight of xylene and then 80 parts by weight of machine oil were added to the solution and the mixture was filtered to give an oil-based preparation.

EXAMPLE 7

Acaricidal Activity Against the Two-spotted Spider Mite (*Tetranychus urticae*)

A 3% by weight emulsifiable concentrate was prepared by the method described in Example 5. The concentrate was then diluted with water to give the concentration of active compound shown in Table 2. Cowpea leaflet containing female adults of *Tetranychus urticae* was sprayed with the test solution in an amount of 5 cc per 2 leaflets using a sprayer of the Mizuho type (obtainable from Mizuho Rikagaku Kikai Co. Limited). The leaflet was air-dried and left standing in a thermostatically controlled room at 25° C. for 72 hours, after which the mortality of the mites was calculated. The number of adults was from 30 to 35 per leaflet and two leaflets were used in each test.

The experiment was carried out using Compound B-41D, and, as controls, milbemycins $\alpha_1$ and $\alpha_3$ (B-41A$_3$ and A$_4$ of our British Patent Specification No. 1,390,336) and the known agricultural miticide Kelthane [a trade mark for a material based on 1,1-bis(-chlorophenyl)-2,2,2- trichloroethanol). The results are shown in Table 2, expressed as the percentage mortality of the adults.

TABLE 2

| Test | Concentration of test solutions (ppm) | | | | |
|---|---|---|---|---|---|
| Compound | 30 | 10 | 3 | 1 | 0.3 |
| Compound B-41D | 100 | 100 | 100 | 89 | 32 |
| Milbemycin $\alpha_1$ | 100 | 85 | 43 | 11 | 0 |
| Milbemycin $\alpha_3$ | 100 | 90 | 45 | 8 | 1 |
| Kelthane | 74 | 25 | 3 | — | — |

EXAMPLE 8

Acaricidal Activity Against Eggs of the Two-spotted Spider Mite (*Tetranychus urticae*)

1-day old eggs of *Tetranychus urticae*, which had previously been oviposited on cowpea leaflet were used in this test. The leaflet was treated with the compound of the invention and the other compounds as described in Example 7. The number of eggs were about 100 per leaflet. 2 weeks after treatment, the number of eggs which failed to hatch were counted and the results are reported in Table 3 as a percentage of the total number of eggs.

TABLE 3

| Test | Concentration of test solution (ppm) | | | | |
|---|---|---|---|---|---|
| Compound | 30 | 10 | 3 | 1 | 0.3 |
| Compound B-41D | 100 | 100 | 96 | 52 | 10 |
| Milbemycin $\alpha_1$ | 98 | 85 | 60 | 30 | 0 |
| Milbemycin $\alpha_3$ | 93 | 89 | 55 | 20 | 5 |
| Kelthane | 19 | 0 | 0 | — | — |

EXAMPLE 9

Acaricidal Activity Against the Citrus Red Mite
(*Panonychus citri*)

The procedure followed was as described in Example 7, except that mulberry leaves bearing female adults of the citrus red mite were used. The results are shown in Table 4.

TABLE 4

| Test | Concentration of test solution (ppm) | | | | | |
|---|---|---|---|---|---|---|
| Compound | 10 | 3 | 1 | 0.3 | 0.1 | 0.03 |
| Compound B-41D | 100 | 100 | 100 | 95 | 90 | 50 |
| Milbemycin $\alpha_1$ | 100 | 98 | 82 | 68 | 55 | 3 |
| Milbemycin $\alpha_3$ | 100 | 95 | 82 | 70 | 48 | 7 |
| Kelthane | 75 | — | — | — | — | — |

In addition to the results reported in Table 4, an emulsion of Kelthane was also tested at a concentration of 30 ppm, but even at this concentration, the mortality rate was only 93%.

It is clear from the these results that Compound B-41D has an extremely high acaricidal activity compared with milbemycins $\alpha_1$ and $\alpha_3$, which, in turn, are substantially better than the known acaricide Kelthane.

EXAMPLE 10

Anthelmintic Activity Against *Nematospiroides dubius*

Four week old male mice of the RFVL strain, each weighing about 18 to 22 g, were orally infected with *Nematospiroides dubius*. The mice were then divided into groups containing five animals and each fed with a feed containing the test compound in the amount shown in Table 5 for 7 days after infection, after which they were given untreated food. 14 days after infection, the animals were sacrificed and the number of parasites in the small intestine was counted and compared with a control group which had been similarly infected but not treated. The results, expressed as anthelmintic activity are shown in Table 5.

TABLE 5

| Test Compound | Amount in feed | Anthelmintic activity |
|---|---|---|
| Compound B-41D | 0.05% | 100% |
|  | 0.005% | 100% |
|  | 0.0005% | 96% |
| Mixture of Milbemycins $\alpha_2$ and $\alpha_4$ | 0.03% | 32% |
| Mixture of Milbemycins $\alpha_1$-$\alpha_6$, $\alpha_9$, $\alpha_{10}$ and $\beta_1$ | 0.03% | 27.6% |

The results shown in Table 5 demonstrate that Compound B-41D has an anthelmintic effect some two orders of magnitude greater than the mixtures of milbemycins with which it is compared.

EXAMPLE 11

Anthelmintic Activity Against *Toxocara cati*

The animals used in this test were 18 kittens (3 males and 15 females) having a body weight of 1.6-3.0 kg and naturally infected with *Toxocara cati*. Each of the kittens was given orally a single dose of Compound B-41D dispersed in olive oil in the following amounts: 2 kittens were given 5 mg/kg body weight of the compound; 3 kittens were given 2.5 mg/kg; 2 kittens were given 1 mg/kg; 3 kittens were given 0.5 mg/kg; 3 kittens were given 0.25 mg/kg; 2 kittens were given 0.1 mg/kg; and 3 kittens were given 0.05 mg/kg. Prior to treatment, the EPG (i.e. number of eggs per gram of feces) was 150-16,250. One week after the treatment, the EPG was zero in all kittens and the total number of worms expelled during that week was 2-40. On autopsy, all kittens were found to be completely free from worms.

EXAMPLE 12

Anthelmintic Activity Against *Toxocara canis*

The animals used in this test were 13 puppies (3 males and 10 females) of body weight 1.2-13.7 kg, which were naturally infected with *Toxocara canis*. Each puppy was given orally a single dose of Compound B-41D dispersed in olive oil in the following amounts: 1 puppy was given a dose of 5 mg/kg body weight; 2 puppies were given 0.25 mg/kg; 4 puppies were given 0.1 mg/kg; 3 puppies were given 0.05 mg/kg; 2 puppies were given 0.025 mg/kg; and 1 puppy was given 0.01 mg/kg. Prior to treatment, the EPG was 100-18,400. One week after treatment, the EPG was zero in all puppies and the total number of worms expelled during that week was 2-36 per puppy. On autopsy, all puppies were found to be completely free from worms.

EXAMPLE 13

Anthelmintic Activity Against *Trichuris vulpis*

The animals used in this test were 5 dogs (2 females and 3 males) of body weight 6.2-11.5 kg and aged 2 or 3 years. Each animal was given orally a single dose of 1 or 5 mg/kg body weight of Compound B-41D in the form of a gelatin-coated capsule. These dogs had been found to be naturally infected with *Trichuris vulpis*. Prior to treatment, the EPG was 100-3,500. One week after treatment, the EPG was 0-200 and the total number of worms expelled during that week was 8-451. On autopsy, the number of worms remaining was 0-33, representing a percentage clearance of 92-100%. It is well-known that infections of *Trichuris vulpis* in the caecum are very difficult to combat and thus the high percentage clearance achieved with a single, relatively mild dose of the compound of the invention indicates an extremely effective and valuable activity against this parasite.

EXAMPLE 14

Anthelmintic Activity Against *Ancylostoma canium*

The animals used in this test were 5 dogs (2 females and 3 males) of body weight 7.0-11.5 kg and aged 2 or 3 years. All of the dogs had been found to be naturally infected with *Ancylostoma canium*. Each of the dogs was given orally a single dose of Compound B-41D in the form of a gelatin-coated capsule and in the following amounts: 2 dogs were given 0.5 mg/kg body weight; 2 dogs were given 1 mg/kg; and 1 dog was given 5 mg/kg. Prior to treatment, the EPG was 200-1,550. One week after treatment, the EPG was zero in all dogs and the total number of worms expelled during that week was 4-82 per dog. On autopsy, all dogs were found to be completely free from worms.

We claim:

1. A process for preparing Compound B-41D having the formula

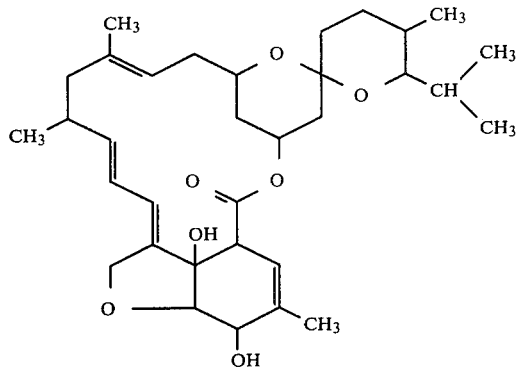

which comprises cultivating Streptomyces strain B-41-146 or a compound B-41D-producing mutant thereof in a culture medium therefor containing skimmed milk to form the Compound B-41D and isolating the Compound B-41D.

2. A process as claimed in claim 1, wherein said culture medium comprises, as a source of assimilible carbon, glucose in an amount up to 8% w/v.

3. A process as claimed in claim 2, wherein said amount of glucose is from 6 to 8% w/v.

4. A process as claimed in claim 2, wherein said culture medium additionally comprises from 0.5 to 2% w/v of one or more carbon sources selected from lactose, maltose and corn starch.

5. A process as claimed in claim 1, wherein said culture medium comprises soybean meal as an additional nitrogen source.

6. A process as claimed in claim 5, wherein the amount of soybean meal is from 0.5 to 1% w/v and the amount of skimmed milk is from 1 to 2% w/v of the culture medium.

7. A process for the preparation of Compound B-41D of the formula

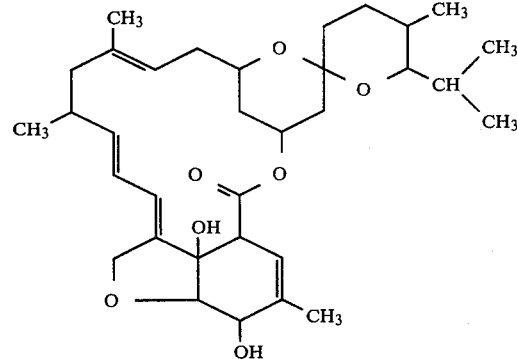

which comprises cultivating Streptomyces strain B-41-146 or a compound B-41D-producing mutant thereof in a culture medium containing from 1 to 2% w/v skimmed milk and further comprising from 6 to 8% w/v glucose; from 0.5 to 2% w/v of one or more carbon sources selected from the group consisting of lactose, maltose and corn starch and from 0.5 to 1% w/v soybeam meal to produce Compound B-41D and isolating said Compound B-41D.

8. A process for the preparation of an acaricidal and anthelmintic composition containing Compound B-41D having the formula

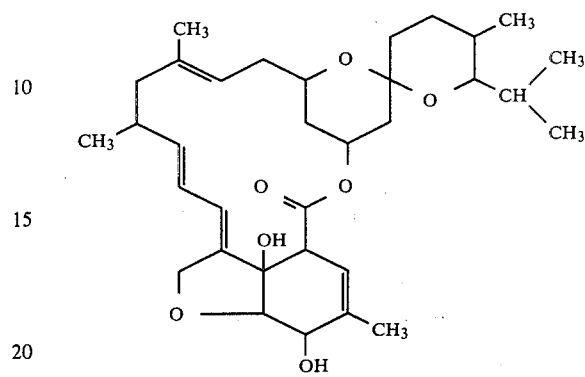

which process comprises the steps:
(a) cultivating Streptomyces strain B-41D compound B-41D-producing mutant thereof in a culture medium therefor containing skimmed milk to produce Compound B-41D;
(b) separating an acaricidally and anthelmintically active fraction containing Compound B-41D from the culture medium; and
(c) concentrating and isolating said Compound B-41D.

9. A process for preparing Compound B-41D having the formula

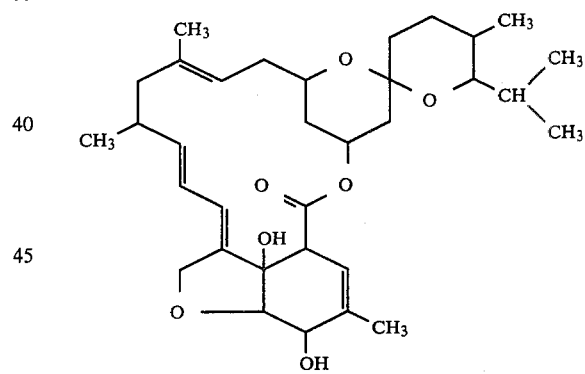

which comprises cultivating Streptomyces strain B-41-146 or a compound B-41D-producing mutant thereof in a culture medium to produce the compound B-41D together with other compounds, extracting compound B-41D together with other compounds from said culture medium, and isolating said compound B-41D.

10. The process as claimed in claim 9 wherein the compound B-41D together with other compounds are solvent extracted from said culture medium.

11. The process as claimed in claim 9 or 10 wherein said compound B-41D is chromatographically isolated from said other compounds.

* * * * *

UNITED STATES PATENT AND TRADEMARK OFFICE
CERTIFICATE OF CORRECTION

PATENT NO. : 4,346,171

DATED : August 24, 1982

INVENTOR(S) : YO TAKIGUCHI et al

It is certified that error appears in the above—identified patent and that said Letters Patent is hereby corrected as shown below:

Column 4, line 24: replace "20400" with --29400--.

Column 11, line 20: replace "hexanes" with --hexane--.

Signed and Sealed this

Nineteenth Day of July 1983

[SEAL]

Attest:

GERALD J. MOSSINGHOFF

Attesting Officer    Commissioner of Patents and Trademarks